United States Patent
De Nanteuil et al.

(10) Patent No.: US 7,439,263 B2
(45) Date of Patent: Oct. 21, 2008

(54) PYRROLIDINE AND THIAZOLIDINE COMPOUNDS

(75) Inventors: Guillaume De Nanteuil, Suresnes (FR); Alain Benoist, Franconville (FR); Murielle Combettes, Maisons Laffite (FR); Elizabeth Harley, Vaureal (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 570 days.

(21) Appl. No.: 11/131,510

(22) Filed: May 18, 2005

(65) Prior Publication Data

US 2005/0261501 A1    Nov. 24, 2005

(30) Foreign Application Priority Data

May 19, 2004    (FR) .................................. 04 05454

(51) Int. Cl.
 *A61K 31/40* (2006.01)
 *C07D 207/04* (2006.01)

(52) U.S. Cl. ....................................... 514/409; 548/407

(58) Field of Classification Search ................. 548/407; 514/409

See application file for complete search history.

(56) References Cited

U.S. PATENT DOCUMENTS

| 6,110,949 | A | 8/2000 | Villhauer |
| 7,138,416 | B2 * | 11/2006 | Sankaranarayanan ....... 514/326 |
| 7,157,490 | B2 * | 1/2007 | Colandrea et al. ........... 514/423 |
| 7,262,207 | B2 * | 8/2007 | Madar et al. ................. 514/326 |
| 2005/0256166 | A1 | 11/2005 | Nakai et al. |

FOREIGN PATENT DOCUMENTS

| WO | WO 98/19998 | 5/1998 |
| WO | WO 01/96295 | 12/2001 |
| WO | WO 03/057144 | 7/2003 |
| WO | WO 03/74500 | 9/2003 |
| WO | WO 2004/016587 | 2/2004 |

OTHER PUBLICATIONS

Villhauer, et al., *J. Med. Chem.*, 2003, 46, 2774-2789.

* cited by examiner

*Primary Examiner*—Golam M Shameem
(74) *Attorney, Agent, or Firm*—Hueschen and Sage

(57) ABSTRACT

Compounds of formula (I):

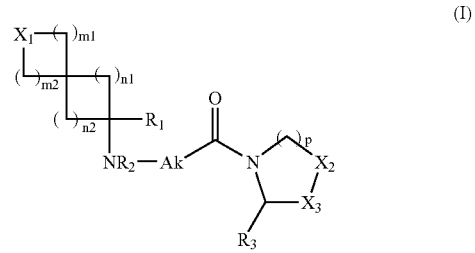

wherein:
 $X_1$ represents an atom or group selected from $CR_{4a}R_{4b}$, O, $S(O)_{q1}$ and $NR_5$, wherein $R_{4a}$, $R_{4b}$, $q_1$ and $R_5$ are as defined in the description,
 $m_1$ represents zero or an integer from 1 to 4 inclusive,
 $m_2$ represents an integer from 1 to 4 inclusive,
 $n_1$ and $n_2$, which may be identical or different, each represent an integer from 1 to 3 inclusive,
 $R_1$ represents hydrogen or a group selected from carboxy, alkoxycarbonyl, optionally substituted carbamoyl and optionally substituted alkyl,
 $R_2$ represents hydrogen or alkyl,
 Ak represents an optionally substituted alkylene chain,
 p represents zero, 1 or 2,
 $R_3$ represents hydrogen or cyano,
 $X_2$ and $X_3$, which may be identical or different, each represent either $S(O)_{q2}$, or $CR_{6a}R_{6b}$, wherein $q_2$, $R_{6a}$ and $R_{6b}$ are as defined in the description,
its optical isomers, where they exist, and its addition salts with a pharmaceutically acceptable acid.

Medicinal products containing the same which are useful as DPP-IV inhibitors.

21 Claims, No Drawings

PYRROLIDINE AND THIAZOLIDINE COMPOUNDS

BACKGROUND OF THE INVENTION

Dipeptidyl-peptidase IV is a membrane serine protease present in numerous human tissues and involved in numerous pathologies:

In particular, DPP IV has been shown to be responsible for inactivation of GLP-1 (glucagon-like peptide-1). GLP-1, being an important stimulator of the secretion of insulin in the pancreas, has a direct beneficial effect on the level of glucose in the blood. Inhibition of DPP IV accordingly represents an extremely promising approach in the treatment of glucose intolerance and of disorders associated with hyperglycaemia such as, for example, non-insulin-dependent diabetes (type II diabetes) or obesity.

DESCRIPTION OF THE PRIOR ART

DPP IV-inhibitors have already been described in the literature, in particular amide compounds in Patent Application EP 0 490 379 and in the journal Adv. Exp. Med. Biol. 1997, 421, 157-160, carbamate compounds in Patent Application DE 19826972, α-amino acid compounds in Patent Application EP 1 258 476 and sulphone compounds in Patent Application EP 1 245 568.

DETAILED DESCRIPTION OF THE INVENTION

The compounds of the invention have dipeptidyl-peptidase IV-inhibiting properties, making them particularly useful for the treatment of glucose intolerance and of disorders associated with hyperglycaemia.

More specifically, the present invention relates to the compounds of formula (I):

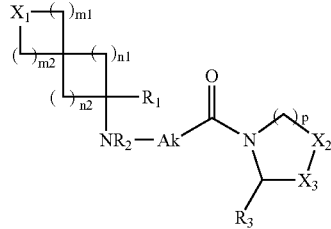

(I)

wherein:
- $X_1$ represents an atom or group selected from $CR_{4a}R_{4b}$, O, $S(O)_{q1}$ and $NR_5$, wherein $R_{4a}$ and $R_{4b}$, which may be identical or different, each represent a hydrogen atom or a linear or branched $C_1$-$C_6$alkyl group,
  or $R_{4a}$ and $R_{4b}$ together form, with the carbon atom carrying them, a $C_3$-$C_7$cycloalkyl group,
- $q_1$ represents zero, 1 or 2,
- and $R_5$ represents a hydrogen atom or a linear or branched $C_1$-$C_6$alkyl group optionally substituted by a hydroxy group,
- $m_1$ represents zero or an integer of from 1 to 4 inclusive,
- $m_2$ represents an integer of from 1 to 4 inclusive,
- $n_1$ and $n_2$, which may be identical or different, each represent an integer of from 1 to 3 inclusive,
- $R_1$ represents a hydrogen atom or a group selected from carboxy, linear or branched $C_1$-$C_6$alkoxycarbonyl, carbamoyl optionally substituted by 1 or 2 linear or branched $C_1$-$C_6$alkyl groups, and linear or branched $C_1$-$C_6$alkyl optionally substituted by a hydroxy group or by an amino group optionally substituted by 1 or 2 linear or branched $C_1$-$C_6$alkyl groups,
- $R_2$ represents a hydrogen atom or a linear or branched $C_1$-$C_6$alkyl group,
- Ak represents a linear or branched $C_1$-$C_4$alkylene chain optionally substituted by one or more halogen, preferably fluorine, atoms,
- p represents zero, 1 or 2,
- $R_3$ represents a hydrogen atom or a cyano group,
- $X_2$ and $X_3$, which may be identical or different, each represent either a $S(O)_{q2}$ group, wherein $q_2$ represents zero, 1 or 2, or a $CR_{6a}R_{6b}$ group, wherein $R_{6a}$ and $R_{6b}$, which may be identical or different, each represent a hydrogen atom or a halogen, preferably fluorine, atom, or $R_{6a}$ represents a hydrogen atom and $R_{6b}$ represents a hydroxy group, to their optical isomers, where they exist, and to addition salts thereof with a pharmaceutically acceptable acid.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid.

$X_1$ preferably represents an oxygen atom or a —$CH_2$— group.

$m_1$ and $m_2$ preferably each represent 1 or 2.

$n_1$ and $n_2$ preferably each represent 1 or 2, and are preferably identical.

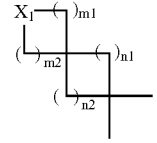

preferably represents a group selected from

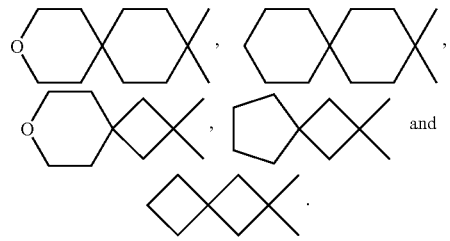

$R_2$ preferably represents a hydrogen atom.
Ak preferably represents a —$CH_2$— group.
p preferably represents 1.
$R_3$ preferably represents a cyano group. In that case, the configuration of the carbon carrying it is preferably (S) when $X_2$ and $X_3$ each represent a $CR_{6a}R_{6b}$ group, and (R) when $X_2$ or $X_3$ represents a $S(O)_{q2}$ group.
$X_2$ and $X_3$ preferably each represent a $CR_{6a}R_{6b}$ group.

Preferred compounds of formula (I) are:
- (2S)-1-({[9-(hydroxymethyl)-3-oxaspiro[5.5]undec-9-yl]amino}acetyl)-2-pyrrolidinecarbonitrile, and its addition salts with a pharmaceutically acceptable acid;
- (2S)-1-({[3-(hydroxymethyl)spiro[5.5]undec-3-yl]amino}acetyl)-2-pyrrolidine-carbonitrile, and its addition salts with a pharmaceutically acceptable acid;
- (2S)-1-({[2-(hydroxymethyl)spiro[3.4]oct-2-yl]amino}acetyl)-2-pyrrolidine-carbonitrile, and its addition salts with a pharmaceutically acceptable acid;
- (4R)-3-[(spiro[5.5]undec-3-ylamino)acetyl]-1,3-thiazolidine-4-carbonitrile, and its addition salts with a pharmaceutically acceptable acid;

2-({2-[(2S)-2-cyanopyrrolidinyl]-2-oxoethyl}amino) spiro[3.3]heptane-2-carboxamide, and its addition salts with a pharmaceutically acceptable acid;

(2S)-1-({[(2-(hydroxymethyl)-7-oxaspiro[3.5]non-2-yl]amino}acetyl)-2-pyrrolidinecarbonitrile, and its addition salts with a pharmaceutically acceptable acid;

(2S,4S)-4-fluoro-1-({[9-(hydroxymethyl)-3-oxaspiro[5.5]undec-9-yl]amino}-acetyl)-2-pyrrolidinecarbonitrile, its (2S,4R) isomer, its (2R,4R) isomer and addition salts thereof with a pharmaceutically acceptable acid;

(2S)-4,4-difluoro-1-({[9-(hydroxymethyl)-3-oxaspiro[5.5]undec-9-yl]amino}-acetyl)-2-pyrrolidinecarbonitrile, and its addition salts with a pharmaceutically acceptable acid;

and (4R)-3-({[9-(hydroxymethyl)-3-oxaspiro[5.5]undec-9-yl]amino}acetyl)-1,3-thiazolidine-4-carbonitrile, and its addition salts with a pharmaceutically acceptable acid.

The invention relates also to a process for the preparation of compounds of formula (I) starting from a compound of formula (II):

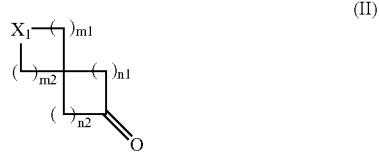

(II)

wherein $X_1$, $m_1$, $m_2$, $n_1$ and $n_2$ are as defined for formula (I), which is converted to a compound of formula (III)

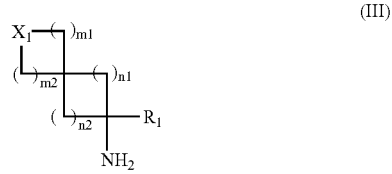

(III)

wherein $X_1$, $m_1$, $m_2$, $n_1$, $n_2$ and $R_1$ are as defined for formula (I), which is reacted with a compound of formula (IV):

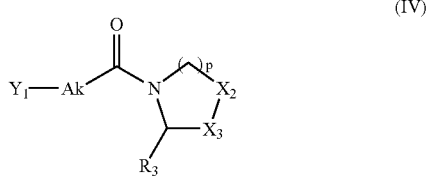

(IV)

wherein Ak, p, $R_3$, $X_2$ and $X_3$ are as defined for formula (I) and $Y_1$ represents a leaving group, to yield compounds of formula (Ia), a particular case of the compounds of formula (I) wherein $R_2$ represents a hydrogen atom:

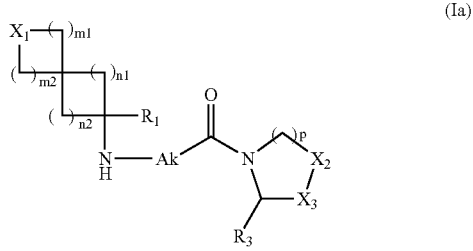

(Ia)

wherein $X_1$, $m_1$, $m_2$, $n_1$, $n_2$, $R_1$, Ak, p, $R_3$, $X_2$ and $X_3$ are as defined for formula (I), which, when it is desired to obtain compounds of formula (I) wherein $R_2$ is other than a hydrogen atom, is reacted with a compound of formula (V):

$$Y_2 - R'_2 \qquad (V)$$

wherein $Y_2$ represents a leaving group and $R'_2$ represents a linear or branched $C_1$-$C_6$-alkyl group, to yield compounds of formula (Ib), a particular case of the compounds of formula (I) wherein $R_2$ represents a linear or branched $C_1$-$C_6$alkyl group:

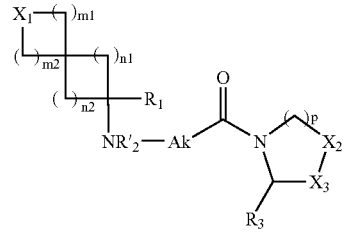

(Ib)

wherein $X_1$, $m_1$, $m_2$, $n_1$, $n_2$, $R_1$, Ak, p, $R_3$, $X_2$ and $X_3$ are as defined for formula (I) and $R'_2$ is as defined hereinbefore, which compounds of formulae (Ia) and (Ib), which constitute the totality of the compounds of formula (I), are purified according to a conventional purification technique, are optionally separated into their optical isomers according to a conventional separation technique and, if desired, are converted into addition salts with a pharmaceutically acceptable acid.

The compounds of formula (IV) can be prepared according to the process described in *J. Med. Chem.* 2002, Vol. 45(12), 2362-2365.

When it is desired to obtain compounds of formula (I) wherein $R_1$ represents a hydrogen atom, the compound of formula (II) is reacted with hydroxylamine to yield a compound of formula (VI):

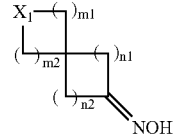

(VI)

wherein $X_1$, $m_1$, $m_2$, $n_1$ and $n_2$ are as defined for formula (I), which is then hydrogenated to a compound of formula (IIIa), a particular case of the compounds of formula (III) wherein $R_1$ represents a hydrogen atom:

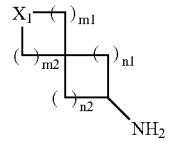

(IIIa)

wherein $X_1$, $m_1$, $m_2$, $n_1$ and $n_2$ are as defined for formula (I).

When it is desired to obtain compounds of formula (I) wherein $R_1$ represents a hydroxymethyl, carboxy or alkoxycarbonyl group, the compound of formula (II) is reacted with ammonium carbonate and potassium cyanide to yield a compound of formula (VII):

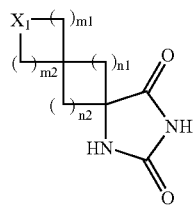
(VII)

wherein $X_1$, $m_1$, $m_2$, $n_1$ and $n_2$ are as defined for formula (I), which is heated with barium sulphate to yield a compound of formula (IIIb), a particular case of the compounds of formula (III) wherein $R_1$ represents a carboxy group:

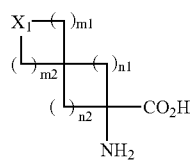
(IIIb)

wherein $X_1$, $m_1$, $m_2$, $n_1$ and $n_2$ are as defined for formula (I), which is esterified to a compound of formula (IIIc), a particular case of the compounds of formula (III) wherein $R_1$ represents an alkoxycarbonyl group:

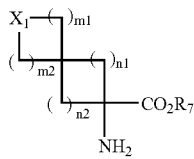
(IIIc)

wherein $X_1$, $m_1$, $m_2$, $n_1$ and $n_2$ are as defined for formula (I) and $R_7$ represents a linear or branched $C_1$-$C_6$ alkyl group, the reduction of which yields a compound of formula (IIId), a particular case of the compounds of formula (III) wherein $R_1$ represents a hydroxymethyl group:

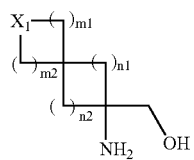
(IIId)

wherein $X_1$, $m_1$, $m_2$, $n_1$ and $n_2$ are as defined for formula (I).

When it is desired to obtain compounds of formula (I) wherein $R_1$ represents a 1-hydroxy-1-methylethyl group, the compound of formula (IIIc) is, after protection of the amine function, reacted with methylmagnesium iodide to yield, after deprotection of the amine function, a compound of formula (IIIe), a particular case of the compounds of formula (III) wherein $R_1$ represents a 1-hydroxy-1-methylethyl group:

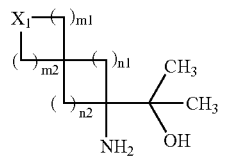
(IIIe)

wherein $X_1$, $m_1$, $m_2$, $n_1$ and $n_2$ are as defined for formula (I).

When it is desired to obtain compounds of formula (I) wherein $R_1$ represents a carbamoyl group, the compound of formula (IIIb) is, after protection of the amine function, reacted with ammonia in the presence of a coupling agent to yield, after deprotection of the amine function, a compound of formula (IIIf), a particular case of the compounds of formula (III) wherein $R_1$ represents a carbamoyl group:

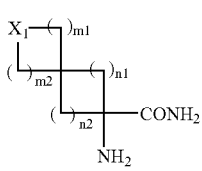
(IIIf)

wherein $X_1$, $m_1$, $m_2$, $n_1$ and $n_2$ are as defined for formula (I).

The compounds of formula (II) can be obtained starting from a compound of formula (VIII):

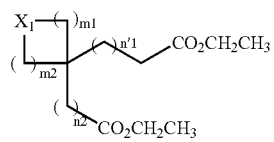
(VIII)

wherein $X_1$, $m_1$, $m_2$ and $n_2$ are as defined hereinbefore and $n'_1$ represents zero, 1 or 2, which is placed in the presence of a base, such as sodium hydride, to yield a compound of formula (IX):

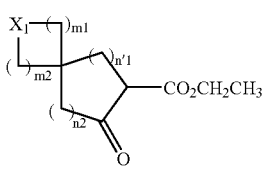
(IX)

wherein $X_1$, $m_1$, $m_2$, $n'_1$ and $n_2$ are as defined hereinbefore, the reaction of which with potassium hydroxide yields a compound of formula (II).

The compounds of formula (IIa), a particular case of the compounds of formula (II) wherein $n_1$ and $n_2$ are identical and each represent 1, can also be obtained starting from a compound of formula (X):

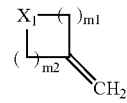
(X)

wherein $X_1$, $m_1$ and $m_2$ are as defined for formula (I), which is reacted with trichloroacetic acid chloride and zinc to yield a compound of formula (XI):

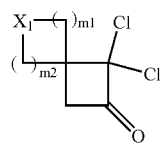
(XI)

wherein $X_1$, $m_1$ and $m_2$ are as defined for formula (I), the reduction of which yields a compound of formula (IIa):

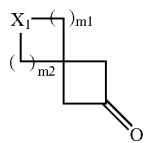
(IIa)

wherein $X_1$, $m_1$ and $m_2$ are as defined for formula (I).

The compounds of formula (IIb), a particular case of the compounds of formula (II) wherein $n_1$ and $n_2$ are identical and each represent 2, can also be obtained starting from a compound of formula (XII):

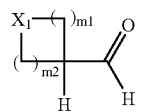
(XII)

wherein $X_1$, $m_1$ and $m_2$ are as defined for formula (I), which is reacted with methyl vinyl ketone to yield a compound of formula (XIII):

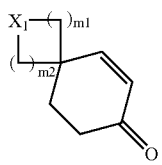
(XIII)

wherein $X_1$, $m_1$ and $m_2$ are as defined for formula (I), the catalytic hydrogenation of which yields a compound of formula (IIb):

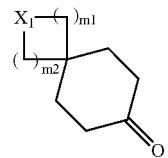
(IIb)

wherein $X_1$, $m_1$ and $m_2$ are as defined for formula (I).

In addition to the fact that they are new, the compounds of the present invention have valuable pharmacological properties. They have dipeptidyl-peptidase IV-inhibiting properties, making them useful in the treatment of glucose intolerance and disorders associated with hyperglycaemia, such as type II diabetes or obesity.

The invention extends also to pharmaceutical compositions comprising as active ingredient at least one compound of formula (I) with one or more appropriate, inert, non-toxic excipients. Amongst the pharmaceutical compositions according to the invention there may be mentioned more especially those which are suitable for oral, parenteral (intravenous, intramuscular or subcutaneous) or nasal administration, tablets or dragees, sublingual tablets, gelatin capsules, lozenges, suppositories, injectable preparations, drinkable suspensions.

The useful dosage is adaptable in accordance with the nature and severity of the disorder, the administration route and also the age and weight of the patient and any associated treatments. The dosage ranges from 0.5 mg to 2 g per 24 hours in one or more administrations.

The Examples which follow illustrate the invention.

The starting materials used are known products or products prepared according to known procedures.

The structures of the compounds described in the Examples were determined according to customary spectrometric techniques (infra-red, NMR, mass spectrometry).

A compound having a (2RS) configuration is understood as being a racemic mixture of compounds of configurations (2R) and (2S).

EXAMPLE 1

(2S)-1-({[9-(Hydroxymethyl)-3-oxaspiro[5.5]undec-9-yl]amino}-acetyl)-2-pyrrolidinecarbonitrile Step A: 3-Oxaspiro[5.5]undec-7-en-9-one 0.5 ml of sulphuric acid is added to 317 mmol of tetrahydro-2H-pyran-4-carboxaldehyde and 317 mmol of methyl vinyl ketone in 500 ml of benzene. The reaction mixture is then refluxed for 3 hours, water being removed using a Dean-Stark apparatus, and then a further 317 mmol of methyl vinyl ketone are added and reflux is continued for 3 hours. The mixture is subsequently washed, dried and then concentrated, and the residue obtained is distilled to yield the expected product.

Step B: 3-Oxaspiro[5.5]undecan-9-one 147.4 mmol of the compound obtained in the above Step are hydrogenated for 15 hours, at ambient temperature and 4.6 bar, in 100 ml of ethyl acetate in the presence of a catalytic amount of 10% Pd/C.

The catalyst is then filtered off, and rinsing with ethyl acetate and concentration are carried out to yield the expected product.

Step C: 11-Oxa-1,3-diazadispiro[4.2.5.2]pentadecane-2,4-dione 165 ml of aqueous 60% ethanol and 480 mmol of ammonium carbonate are added to 300 mmol of the compound obtained in the above Step. The reaction mixture is then heated to 55° C., 5.3 g of potassium cyanide in 40 ml of water are subsequently added in the course of 5 min., and the mixture is stirred for 2 hours at 55° C. The ethanol is then evaporated off and the mixture is subsequently filtered; the cake is rinsed with water and with acetone and then dried to yield the expected product in the form of a flaky white solid.

Step D: 9-Amino-3-oxaspiro[5.5]undecane-9-carboxylic acid hydrochloride

In a 1-litre autoclave, 177.8 mmol of barium sulphate are added to 88.9 mmol of the compound obtained in the above Step in 335 ml of water. The mixture is then heated overnight at 160° C. and subsequently cooled in an ice bath. The barium carbonate formed is filtered off and rinsed with water, and carbon dioxide is bubbled into the aqueous phase. The aqueous phase is then filtered again, and the filtrate is subsequently concentrated to dryness to yield the expected product in the form of a powder.

Step E: Methyl 9-amino-3-oxaspiro[5.5]undecane-9-carboxylate hydrochloride 100 ml of methanol are added to 61.3 mmol of the compound obtained in the above Step. The resulting suspension is cooled to 5° C. and then 184 mmol of thionyl chloride are added dropwise. The reaction mixture is subsequently stirred for 1 hour at 20° C. and then for 2 hours at reflux, before being evaporated to dryness to yield the expected product in the form of a powder.

Step F:
(9-Amino-3-oxaspiro[5.5]undec-9-yl)methanol 6.8 g of lithium aluminium hydride, and then 59.7 mmol of the compound obtained in the above Step in the form of a base in solution in 75 ml of tetrahydrofuran, are added at 0° C. to 50 ml of tetrahydrofuran. The reaction mixture is subsequently stirred for 30 min. at 0° C. and then overnight at 20° C.

It is subsequently cooled to 5° C. and there are then added 6.8 ml of water, 6.8 ml of 15% sodium hydroxide solution and 3×6.8 ml of water. The mixture is stirred vigorously for 20 min. and then filtered over Celite. The precipitate is rinsed with ether and the filtrate is dried and then evaporated to yield the expected product in the form of a solid.

Step G: (2S)-1-({[9-(Hydroxymethyl)-3-oxaspiro[5.5]undec-9-yl]amino}acetyl)-2-pyrrolidinecarbonitrile 90 ml of dichloromethane, 6 mmol of (2S)-1-(chloroacetyl)-2-pyrrolidinecarbonitrile and then 24 mmol of potassium carbonate are added to 12 mmol of the compound obtained in the above Step. After stirring for 6 days at 20° C., the precipitate formed is filtered off and rinsed with dichloromethane, and the filtrates are concentrated to dryness. The residue obtained is purified by chromatography on silica (eluant: dichloromethane/methanol 97/3) to yield the expected product in the form of a yellow oil which solidifies in the cold to yield a white powder.

Elemental Microanalysis:

|  | % C | % H | % N |
|---|---|---|---|
| Calculated | 64.45 | 8.71 | 12.53 |
| Found | 64.50 | 8.78 | 12.28 |

EXAMPLE 2

(2S)-1-[(Spiro[5.5]undec-3-ylamino)acetyl]-2-pyrrolidinecarbonitrile hydrochloride Step A: Spiro[5.5]undecan-3-one The expected product is obtained according to the procedure described in Steps A and B of Example 1, with the replacement of tetrahydro-2H-pyran-4-carboxaldehyde with cyclohexanecarboxaldehyde in Step A.

Step B: Spiro[5.5]undecan-3-one oxime 70 ml of pyridine and 3.45 g of hydroxylamine hydrochloride are added to 39 mmol of the compound obtained in the above Step in solution in dioxane. The reaction mixture is then heated at reflux overnight and subsequently concentrated to dryness to yield an oil, which crystallises and which is washed with water to yield the expected product in the form of a powder after filtration and drying.

Step C: Spiro[5.5]undec-3-ylamine 3 ml of concentrated ammonium hydroxide and a catalytic amount of Raney nickel are added to 15.8 mmol of the compound obtained in the above Step in solution in dioxane. The reaction mixture is then hydrogenated overnight at ambient temperature and pressure. The catalyst is subsequently filtered off and rinsed and the solution is concentrated to yield the expected product in the form of an oil.

Step D: (2S)-1-[(Spiro[5.5]undec-3-ylamino)acetyl]-2-pyrrolidinecarbonitrile

The expected product is obtained according to the procedure described in Step G of Example 1, starting from the compound obtained in the above Step and (2S)-1-(chloroacetyl)-2-pyrrolidinecarbonitrile.

Step E: (2S)-1-[(Spiro[5.5]undec-3-ylamino)acetyl]-2-pyrrolidinecarbonitrile hydrochloride The expected product is obtained by converting the compound obtained in the above Step into a salt using hydrochloric acid.

Elemental Microanalysis:

|  | % C | % H | % N | % Cl |
|---|---|---|---|---|
| Calculated | 63.60 | 8.90 | 12.36 | 10.43 |
| Found | 63.66 | 8.92 | 12.18 | 10.23 |

EXAMPLE 3

(2S)-1-[(Spiro[4.5]dec-8-ylamino)acetyl]-2-pyrrolidinecarbonitrile hydrochloride The expected product is obtained according to the procedure of Example 2, with the replacement of cyclohexanecarboxaldehyde with cyclopentanecarboxaldehyde in Step A.

Elemental Microanalysis:

|  | % C | % H | % N | % Cl |
|---|---|---|---|---|
| Calculated | 62.66 | 8.66 | 12.89 | 10.88 |
| Found | 62.58 | 8.76 | 12.92 | 10.97 |

EXAMPLE 4

N-[2-Oxo-2-(1-pyrrolidinyl)ethyl]spiro[5.5]undec-3-ylamine hydrochloride

The expected product is obtained according to the procedure of Example 2, with the replacement of (2S)-1-(chloroacetyl)-2-pyrrolidinecarbonitrile with 1-(chloroacetyl)-pyrrolidine in Step D.

Elemental Microanalysis:

|  | % C | % H | % N | % Cl |
|---|---|---|---|---|
| Calculated | 64.84 | 9.92 | 8.90 | 11.26 |
| Found | 65.54 | 9.89 | 8.98 | 11.28 |

EXAMPLE 5

(2S)-1-({[3-(Hydroxymethyl)spiro[5.5]undec-3-yl]amino}acetyl)-2-pyrrolidinecarbonitrile The expected product is obtained according to the procedure of Example 1, with the replacement of tetrahydro-2H-pyran-4-carboxaldehyde with cyclohexanecarboxaldehyde in Step A.

Elemental Microanalysis:

|  | % C | % H | % N |
|---|---|---|---|
| Calculated | 68.43 | 9.37 | 12.60 |
| Found | 68.78 | 9.32 | 12.45 |

EXAMPLE 6

(2S)-1-[(Spiro[5.7]tridec-3-ylamino)acetyl]-2-pyrrolidinecarbonitrile hydrochloride The expected product is obtained according to the procedure of Example 2, with the replacement of cyclohexanecarboxaldehyde with cyclooctanecarboxaldehyde in Step A.

Elemental Microanalysis:

|  | % C | % H | % N | % Cl |
|---|---|---|---|---|
| Calculated | 65.28 | 9.31 | 11.42 | 9.63 |
| Found | 65.56 | 9.01 | 11.21 | 9.63 |

EXAMPLE 7

(2S)-1-[(3-Oxaspiro[5.5]undec-9-ylamino)acetyl]-2-pyrrolidine-carbonitrile hydrochloride The expected product is obtained according to the procedure described in Steps B to E of Example 2, starting from the compound obtained in Step B of Example 1.

Elemental Microanalysis:

|  | % C | % H | % N | % Cl |
|---|---|---|---|---|
| Calculated | 59.72 | 8.26 | 12.29 | 10.37 |
| Found | 59.79 | 7.96 | 12.16 | 10.96 |

EXAMPLE 8

(2S)-1-[(Dispiro[5.2.5.2]hexadec-3-ylamino)acetyl]-2-pyrrolidine-carbonitrile

The expected product is obtained according to the procedure described in Steps A to D of Example 2, with the replacement of cyclohexanecarboxaldehyde with spiro[5.5]undecane-3-carboxaldehyde in Step A.

Elemental Microanalysis:

|  | % C | % H | % N |
|---|---|---|---|
| Calculated | 74.35 | 10.04 | 11.31 |
| Found | 74.40 | 9.94 | 11.07 |

EXAMPLE 9

(2S)-1-[(Spiro[3.3]hept-2-ylamino)acetyl]-2-pyrrolidinecarbonitrile hydrochloride Step A: 1,1-Dichlorospiro[3.3]heptan-2-one 6.25 g of powdered zinc and then 11 ml of trichloroacetic acid chloride in solution in 170 ml of ether are added to 5 g of methylenecyclobutane in solution in ether. The solution is subjected to sonication for 3 hours while maintaining the temperature at 20° C., and then the black solution is filtered through Whatman filter. The filtrate is washed, dried, filtered and concentrated to yield the expected product in the form of a brown oil.

Step B: Spiro[3.3]heptan-2-one 28 g of the compound obtained in the above Step and then 620 ml of water are added to 420 ml of glacial acetic acid. The reaction mixture is cooled using a cold water bath, and then 28.1 g of powdered zinc are added. After stirring for 20 min., the bath is removed and the reaction mixture is stirred overnight at 20° C. The solution is filtered, extracted with pentane and evaporated. The residue is taken up in pentane and the solution is washed, dried, filtered and concentrated to yield the expected product in the form of a clear yellow liquid.

Step C: (2S)-1-[(Spiro[3.3]hept-2-ylamino)acetyl]-2-pyrrolidinecarbonitrile

The expected product is obtained according to the procedure described in Steps B to D of Example 2, starting from the compound obtained in the above Step.

Step D: (2S)-1-[(Spiro[3.3]hept-2-ylamino)acetyl]-2-pyrrolidinecarbonitrile hydrochloride The expected product is obtained by converting the compound obtained in the above Step into a salt using hydrochloric acid.

Elemental Microanalysis:

|  | % C | % H | % N | % Cl |
|---|---|---|---|---|
| Calculated | 59.25 | 7.81 | 14.81 | 12.49 |
| Found | 59.27 | 7.78 | 14.51 | 12.93 |

EXAMPLE 10

(2S)-1-[(Spiro[5.9]pentadec-3-ylamino)acetyl]-2-pyrrolidine carbonitrile

The expected product is obtained according to the procedure described in Steps A to D of Example 2, with the replacement of cyclohexanecarboxaldehyde with cyclodecane-carboxaldehyde in Step A.

Melting point: 83° C.

EXAMPLE 11

(2S)-1-[(Spiro[3.5]non-7-ylamino)acetyl]-2-pyrrolidinecarbonitrile hydrochloride Step A: Ethyl 7-oxospiro[3.5]nonane-6-carboxylate 20.6 mmol of 3-[1-(ethoxycarbonylethyl)cyclobutyl]propionic acid ethyl ester in solution in tetrahydrofuran are added at 0° C. to 22.7 mmol of 95% sodium hydride in suspension in 15 ml of tetrahydrofuran. The reaction mixture is refluxed for 4 hours and then 49 ml of acetic acid are added. The tetrahydrofuran is evaporated off and the residue obtained is extracted with ethyl acetate. The combined organic phases are washed, filtered, dried and evaporated to yield an oil, which is subjected to chromatography on silica (eluant: dichloromethane/ethyl acetate 95/5) to yield the expected product.

Step B: Spiro[3.5]nonan-7-one 11.1 g of potassium hydroxide in 100 ml of water are added to 39.7 mmol of the compound obtained in the above Step in solution in dioxane. The reaction mixture is refluxed overnight and then, after returning to ambient temperature, is extracted with ether. The combined organic phases are washed, dried, filtered and evaporated to yield the expected product in the form of a volatile oil.

Step C: (2S)-1-[(Spiro[3.5]non-7-ylamino)acetyl]-2-pyrrolidinecarbonitrile hydrochloride The expected product is obtained according to the procedure described in Steps B to E of Example 2, starting from the compound obtained in the above Step.

Elemental Microanaylsis:

|  | % C | % H | % N | % Cl |
|---|---|---|---|---|
| Calculated | 61.62 | 8.40 | 13.47 | 11.37 |
| Found | 61.39 | 8.32 | 13.22 | 11.91 |

EXAMPLE 12

(2S)-1-[(Spiro[3.5]non-2-ylamino)acetyl]-2-pyrrolidinecarbonitrile trifluoroacetate Step A: (2S)-1-[(Spiro[3.5]non-2-ylamino)acetyl]-2-pyrrolidinecarbonitrile The expected product is obtained according to the procedure described in Steps A to C of Example 9, with the replacement of methylenecyclobutane with methylenecyclohexane in Step A.

Step B: (2S)-1-[(Spiro[3.5]non-2-ylamino)acetyl]-2-pyrrolidinecarbonitrile trifluoroacetate The expected product is obtained by converting the compound obtained in the above Step into a salt using trifluoroacetic acid.

Mass spectrometry: [M+H]+=276

EXAMPLE 13

(2S)-1-[(Spiro[5.6]dodec-3-ylamino)acetyl]-2-pyrrolidine-carbonitrile

The expected product is obtained according to the procedure described in Steps A to D of Example 2, with the replacement of cyclohexanecarboxaldehyde with cycloheptane-carboxaldehyde in Step A.

Elemental Microanalysis:

|  | % C | % H | % N |
|---|---|---|---|
| Calculated | 71.88 | 9.84 | 13.24 |
| Found | 71.52 | 9.95 | 13.14 |

EXAMPLE 14

(2S)-1-[(Spiro[3.4]oct-2-ylamino)acetyl]-2-pyrrolidinecarbonitrile hydrochloride Step A: Spiro[3.4]octan-2-one The expected product is obtained according to the procedure described in Steps A and B of Example 9, with the replacement of methylenecyclobutane with methylenecyclopentane in Step A.

Step B: (2S)-1-[(Spiro[3.4]oct-2-ylamino)acetyl]-2-pyrrolidinecarbonitrile hydrochloride The expected product is obtained according to the procedure described in Steps B to E of Example 2, starting from the compound obtained in the above Step.

Elemental Microanalysis:

|  | % C | % H | % N | % Cl |
|---|---|---|---|---|
| Calculated | 60.49 | 8.12 | 14.11 | 11.90 |
| Found | 61.08 | 8.00 | 14.18 | 11.37 |

EXAMPLE 15

(2S)-1-{[(3,3-Dioxo-3-thiaspiro[5.5]undec-9-ylamino)acetyl]-2-pyrrolidinecarbonitrile The expected product is obtained according to the procedure described in Steps A to D of Example 2, with the replacement of cyclohexanecarboxaldehyde with tetrahydro-2H-thiopyran-4-carboxaldehyde 1,1-dioxide in Step A.

---

(Page 13 Elemental Microanalysis:)

|  | % C | % H | % N |
|---|---|---|---|
| Calculated | 73.49 | 10.37 | 11.69 |
| Found | 73.46 | 10.44 | 11.64 |

Elemental Microanalysis:

|  | % C | % H | % N | % S |
|---|---|---|---|---|
| Calculated | 57.76 | 7.70 | 11.89 | 9.07 |
| Found | 57.42 | 7.54 | 11.48 | 8.83 |

EXAMPLE 16

(2S)-1-({[2-(Hydroxymethyl)spiro[3.3]hept-2-yl]amino}acetyl)-2-pyrrolidinecarbonitrile hydrochloride Step A: (2S)-1-({[2-(Hydroxymethyl)spiro[3.3]hept-2-yl]amino}acetyl)-2-pyrrolidinecarbonitrile The expected product is obtained according to the procedure described in Steps C to G of Example 1, with the replacement of 3-oxaspiro[5.5]undecan-9-one in Step C with the compound obtained in Step B of Example 9.

Step B: (2S)-1-({[2-(Hydroxymethyl)spiro[3.3]hept-2-yl]amino}acetyl)-2-pyrrolidinecarbonitrile hydrochloride The expected product is obtained by converting the compound obtained in the above Step into a salt using hydrochloric acid.

Elemental Microanalysis:

|  | % C | % H | % N | % Cl |
|---|---|---|---|---|
| Calculated | 57.41 | 7.71 | 13.39 | 11.30 |
| Found | 57.32 | 8.02 | 13.33 | 11.91 |

EXAMPLE 17

(2S)-1-({[2-(Hydroxymethyl)spiro[3.4]oct-2-yl]amino}acetyl)-2-pyrrolidinecarbonitrile hydrochloride Step A: (2S)-1-({[2-(Hydroxymethyl)spiro[3.4]oct-2-yl]amino}acetyl)-2-pyrrolidinecarbonitrile The expected product is obtained according to the procedure described in Steps C to G of Example 1, with the replacement of 3-oxaspiro[5.5]undecan-9-one in Step C with the compound obtained in Step A of Example 14.

Step B: (2S)-1-({[2-(Hydroxymethyl)spiro[3.4]oct-2-yl]amino}acetyl)-2-pyrrolidinecarbonitrile hydrochloride The expected product is obtained by converting the compound obtained in the above Step into a salt using hydrochloric acid.

Elemental Microanalysis:

|  | % C | % H | % N | % Cl |
|---|---|---|---|---|
| Calculated | 58.62 | 7.99 | 12.82 | 10.81 |
| Found | 58.53 | 7.90 | 12.65 | 10.81 |

EXAMPLE 18

(4R)-3-[(Spiro[5.5]undec-3-yl-amino)acetyl]-1,3-thiazolidine-4-carbonitrile trifluoroacetate Step A: (4R)-3-[(Spiro[5.5]undec-3-yl-amino)acetyl]-1,3-thiazolidine-4-carbonitrile The expected product is obtained according to the procedure described in Step G of Example 1, starting from the compound obtained in Step C of Example 2 and (4R)-3-(chloroacetyl)-1,3-thiazolidine-4-carbonitrile.

Step B: (4R)-3-[(Spiro[5.5]undec-3-yl-amino)acetyl]-1,3-thiazolidine-4-carbonitrile trifluoroacetate The expected product is obtained by converting the compound obtained in the above Step into a salt using trifluoroacetic acid.

Elemental Microanalysis:

|  | % C | % H | % N | % S |
|---|---|---|---|---|
| Calculated | 52.40 | 6.48 | 9.65 | 7.36 |
| Found | 52.10 | 6.54 | 9.42 | 7.19 |

EXAMPLE 19

2-({2-[(2S)-2-Cyanopyrrolidinyl]-2-oxoethyl}amino)spiro[3.3]-heptane-2-carboxamide Step A: 2-Aminospiro[3.3]heptane-2-carboxylic acid The expected product is obtained according to the procedure described in Steps C and D of Example 1, starting from the compound obtained in Step B of Example 9.

Step B: 2-(tert-Butyloxycarbonylamino)spiro[3.3]heptane-2-carboxylic acid 40 ml of dioxane and then, at 0° C., 6.71 g of di(tert-butyl)dicarbonate in dioxane are added to 4.35 g of the compound obtained in the above Step in solution in 11 ml of sodium hydroxide solution. After one night at 20° C., the dioxane is evaporated off and the residue obtained is taken up in water. Extraction is carried out with ether, and then the aqueous phase is acidified to pH 3 using an aqueous 10% citric acid solution. The aqueous phase is extracted with ethyl acetate. The organic phases are combined and washed with brine, dried and concentrated to dryness to yield the expected product in the form of a white paste.

Step C: 2-(tert-Butyloxycarbonylamino)spiro[3.3]heptane-2-carboxamide 811 mg of N-hydroxysuccinimide and 1.45 g of dicyclohexylcarbodiimide are added to 1.8 g of the compound obtained in the above Step in solution in tetrahydrofuran. After one night at 20° C., the reaction mixture is filtered, and gaseous ammonia is bubbled into the filtrate. After one night at 20° C., the reaction mixture is filtered again and concentrated to dryness to yield the expected product in the form of a white powder.

Step D: 2-Aminospiro[3.3]heptane-2-carboxamide hydrochloride 1.84 g of the compound obtained in the above Step are dissolved in ethyl acetate and then gaseous HCl is bubbled through at 0° C. for 10 min. A precipitate appears. After 30 min. at 0° C., the precipitate is filtered off and rinsed with ethyl acetate, and then dried to yield the expected product in the form of a white powder.

Step E: 2-({2-[(2S)-2-Cyanopyrrolidinyl]-2-oxoethyl}amino)spiro[3.3]heptane-2-carboxamide The expected product is obtained according to the procedure described in Step G of Example 1, starting from the compound obtained in the above Step and (2S)-1-(chloroacetyl)-2-pyrrolidinecarbonitrile.

Elemental Microanalysis:

|  | % C | % H | % N |
|---|---|---|---|
| Calculated | 62.05 | 7.64 | 19.30 |
| Found | 62.05 | 7.48 | 19.20 |

EXAMPLE 20

(2S)-1-[(3-Azaspiro[5.5]undec-9-ylamino)acetyl]-2-pyrrolidine-carbonitrile bis(trifluoroacetate)

Step A: 3-Azaspiro[5.5]undecan-9-one

The expected product is obtained according to the procedure described in Steps A and B of Example 1, with the replacement of tetrahydro-2H-pyran-4-carboxaldehyde with benzyl 4-formyl-1-piperidinecarboxylate in Step A.

Step B: tert-Butyl 9-oxo-3-azaspiro[5.5]undecane-3-carboxylate

The expected product is obtained by reaction of the compound obtained in the above Step with di-tert-butyl dicarbonate in accordance with the procedure described in Step B of Example 19.

Step C: tert-Butyl 9-({2-[(2S)-2-cyanopyrrolidinyl]-2-oxoethyl}amino)-3-azaspiro-[5.5]undecane-3-carboxylate The expected product is obtained according to the procedure described in Steps B to D of Example 2, starting from the compound obtained in the above Step.

Step D: (2S)-1-[(3-Azaspiro[5.5]undec-9-ylamino)acetyl]-2-pyrrolidinecarbonitrile bis(trifluoroacetate)

The expected product is obtained by reaction of the compound obtained in the above Step with 30 equivalents of trifluoroacetic acid in dichloromethane at 0-5° C. for 1 hour. The mixture is concentrated to dryness. The compound is purified by preparative HPLC.

Mass spectrometry: [M+H]+=305

EXAMPLE 21

(2S)-1-({[3-(Hydroxymethyl)-9,9-dimethylspiro[5.5]undec-3-yl]-amino}acetyl)-2-pyrrolidinecarbonitrile The expected product is obtained according to the procedure of Example 1, with the replacement of tetrahydro-2H-pyran-4-carboxaldehyde with 4,4-dimethylcyclohexane-carboxaldehyde in Step A.

Elemental Microanalysis:

|  | % C | % H | % N |
|---|---|---|---|
| Calculated | 69.77 | 9.76 | 11.62 |
| Found | 69.54 | 9.72 | 11.43 |

EXAMPLE 22

(2S)-1-({[2-(1-Hydroxy-1-methylethyl)spiro[3.3]hept-2-yl]amino}-acetyl)-2-pyrrolidinecarbonitrile hydrochloride

Step A: Methyl 2-aminospiro[3.3]heptane-2-carboxylate

The expected product is obtained according to the procedure described in Step E of Example 1, starting from the compound obtained in Step A of Example 19.

Step B: Methyl 2-(tert-butyloxycarbonylamino)spiro[3.3]heptane-2-carboxylate 5.8 ml of triethylamine and then, at 0° C., 9.02 g of di(tert-butyl) dicarbonate in dichloromethane, are added to 8.5 g of the compound obtained in the above Step in solution in dichloromethane. After stirring overnight at 20° C., the reaction mixture is washed with an aqueous 10% citric acid solution and then with water. The organic phase is dried, filtered and concentrated to yield the expected product in the form of an orange oil.

Step C: 2-(2-tert-Butyloxycarbonylaminospiro[3.3]hept-2-yl)-2-propanol

There are added to 50 ml of ether 42 ml of a 3M solution of methylmagnesium iodide in ether and then, at 0° C. and dropwise, 5 g of the compound obtained in the above Step in solution in ether. After stirring for 1 hour at 0° C., ammonium chloride is added and then the reaction mixture is stirred for 1 hour at 20° C. The aqueous phase is extracted with ethyl acetate and then the combined organic phases are washed, dried and concentrated to dryness to yield the expected product in the form of an oil which crystallises.

Step D: 2-(2-Aminospiro[3.3]hept-2-yl)-2-propanol trifluoroacetate 40 ml of trifluororacetic acid are added at 0° C. to 4.8 g of the compound obtained in the above Step in solution in dichloromethane. After stirring for 30 min. at 0° C., the reaction mixture is evaporated to dryness and the residue is taken up several times with toluene; the toluene is then evaporated off to yield the expected product in the form of a colourless oil.

Step E: (2S)-1-({[2-(1-Hydroxy-1-methylethyl)spiro[3.3]hept-2-yl]amino}acetyl)-2-pyrrolidinecarbonitrile The expected product is obtained according to the procedure described in Step G of Example 1, starting from the compound obtained in the above Step and (2S)-1-(chloroacetyl)-2-pyrrolidinecarbonitrile.

Step F: (2S)-1-({[2-(1-Hydroxy-1-methylethyl)spiro[3.3]hept-2-yl]amino}acetyl)-2-pyrrolidinecarbonitrile hydrochloride The expected product is obtained by converting the compound obtained in the above Step into a salt using hydrochloric acid.

Elemental Microanalysis:

|  | % C | % H | % N | % Cl |
| --- | --- | --- | --- | --- |
| Calculated | 59.72 | 8.26 | 12.29 | 10.37 |
| Found | 58.96 | 8.48 | 11.95 | 10.99 |

EXAMPLE 23

(2S)-1-[(3-Thiaspiro[5.5]undec-9-ylamino)acetyl]-2-pyrrolidine-carbonitrile hydrochloride Step A: 3-Thiaspiro[5.5]undecan-9-one oxime 3,3-dioxide The expected product is obtained according to the procedure described in Steps A and B of Example 2, with the replacement of cyclohexanecarboxaldehyde with tetrahydro-2H-thiopyran-4-carboxaldehyde 1,1-dioxide in Step A.

Step B: 3-Thiaspiro[5.5]undecan-9-amine 4 g of the compound obtained in the above Step are added in portions to 7.9 g of lithium aluminium hydride in suspension in 200 ml of tetrahydrofuran. The reaction mixture is then refluxed for 12 hours and subsequently hydrolysed by the addition of 8 ml of water, 8 ml of a 15% sodium hydroxide solution and 16 ml of water. The salts obtained are then filtered off and the filtrate is subsequently concentrated to dryness to yield the title product.

Step C: (2S)-1-[(3-Thiaspiro[5.5]undec-9-ylamino)acetyl]-2-pyrrolidinecarbonitrile The expected product is obtained according to the procedure described in Step G of Example 1, starting from the compound obtained in the above Step and (2S)-1-(chloroacetyl)-2-pyrrolidinecarbonitrile.

Step D: (2S)-1-[(3-Thiaspiro[5.5]undec-9-ylamino)acetyl]-2-pyrrolidinecarbonitrile hydrochloride The expected product is obtained by converting the compound obtained in the above Step into a salt using hydrochloric acid.

Elemental Microanalysis:

|  | % C | % H | % N | % S | % Cl |
| --- | --- | --- | --- | --- | --- |
| Calculated | 57.04 | 7.88 | 11.74 | 8.96 | 9.90 |
| Found | 59.67 | 7.96 | 11.56 | 9.14 | 10.52 |

EXAMPLE 24

(2S)-1-({[3-(2-Hydroxyethyl)-3-azaspiro[5.5]undec-9-yl]amino}-acetyl)-2-pyrrolidinecarbonitrile bis(trifluoroacetate)

Step A: 3-Azaspiro[5.5]undecan-9-one

The expected product is obtained according to the procedure described in Steps A and B of Example 1, with the replacement of tetrahydro-2H-pyran-4-carboxaldehyde with benzyl 4-formyl-1-piperidinecarboxylate in Step A.

Step B: 3-(2-Hydroxyethyl)-3-azaspiro[5.5]undecan-9-one

The expected product is obtained by alkylation of the compound obtained in the above Step with 2-bromoethanol in the presence of potassium carbonate.

Step C: (2S)-1-({[3-(2-Hydroxyethyl)-3-azaspiro[5.5]undec-9-yl]amino}acetyl)-2-pyrrolidinecarbonitrile The expected product is obtained according to the procedure described in Steps B to D of Example 2, starting from the compound obtained in the above Step.

Step D (2S)-1-({[3-(2-Hydroxyethyl)-3-azaspiro[5.5]undec-9-yl]amino}acetyl)-2-pyrrolidinecarbonitrile bis(trifluoroacetate)

The expected product is obtained by converting the compound obtained in the above Step into a salt using trifluoroacetic acid.

Elemental Microanalysis:

|  | % C | % H | % N |
| --- | --- | --- | --- |
| Calculated | 47.92 | 5.94 | 9.72 |
| Found | 47.28 | 5.94 | 9.38 |

EXAMPLE 25

(2S)-1-({[2-(Hydroxymethyl)-7-oxaspiro[3.5]non-2-yl]amino}-acetyl)-2-pyrrolidinecarbonitrile Step A: 7-Oxaspiro[3.5]nonan-2-one The expected product is obtained according to the procedure described in Steps A and B of Example 9, with the replacement of methylenecyclobutane with 4-methylenetetrahydro-2H-pyran in Step A.

Step B: (2S)-1-({[2-(Hydroxymethyl)-7-oxaspiro[3.5]non-2-yl]amino}acetyl)-2-pyrrolidinecarbonitrile The expected product is obtained according to the procedure described in Steps C to G of Example 1, starting from the compound obtained in the above Step.

Melting point: 103° C.

Elemental Microanalysis:

|  | % C | % H | % N |
|---|---|---|---|
| Calculated | 62.52 | 8.20 | 13.67 |
| Found | 62.56 | 8.25 | 13.32 |

EXAMPLE 26

(2S)-1-({[2-(Hydroxymethyl)spiro[3.5]non-2-yl]amino}acetyl)-2-pyrrolidinecarbonitrile Step A: Spiro[3.5]nonan-2-one The expected product is obtained according to the procedure described in Steps A and B of Example 9, with the replacement of methylenecyclobutane with methylenecyclohexane in Step A.

Step B: (2S)-1-({[2-(Hydroxymethyl)spiro[3.5]non-2-yl]amino}acetyl)-2-pyrrolidinecarbonitrile The expected product is obtained according to the procedure described in Steps C to G of Example 1, starting from the compound obtained in the above Step.

Elemental Microanalysis:

|  | % C | % H | % N |
|---|---|---|---|
| Calculated | 66.85 | 8.91 | 13.76 |
| Found | 66.66 | 8.55 | 13.65 |

EXAMPLE 27

(2S)-1-[(7-Oxaspiro[3.5]non-2-ylamino)acetyl]-2-pyrrolidine-carbonitrile trifluoroacetate Step A: (2S)-1-[(7-Oxaspiro[3.5]non-2-ylamino)acetyl]-2-pyrrolidinecarbonitrile The expected product is obtained according to the procedure described in Steps A to C of Example 9, with the replacement of methylenecyclobutane with 4-methylenetetrahydro-2H-pyran in Step A.

Step B: (2S)-1-[(7-Oxaspiro[3.5]non-2-ylamino)acetyl]-2-pyrrolidinecarbonitrile trifluoroacetate The expected product is obtained by converting the compound obtained in the above Step into a salt using trifluoroacetic acid.

Elemental Microanalysis:

|  | % C | % H | % N |
|---|---|---|---|
| Calculated | 52.17 | 6.18 | 10.74 |
| Found | 52.15 | 6.35 | 10.73 |

EXAMPLE 28

(2S)-1-[(Spiro[2.5]oct-6-ylamino)acetyl]-2-pyrrolidinecarbonitrile

Step A: Spiro[2.5]octan-6-one

The expected product is obtained according to the procedure described in Steps A and B of Example 11, with the replacement of 3-[1-(ethoxycarbonylethyl)cyclobutyl]propionic acid with 3-[1-(ethoxycarbonylethyl)cyclopropyl]propionic acid in Step A.

Step B: (2S)-1-[(Spiro[2.5]oct-6-ylamino)acetyl]-2-pyrrolidinecarbonitrile

The expected product is obtained according to the procedure described in Steps A to D of Example 2, starting from the compound obtained in the above Step.

Elemental Microanalysis:

|  | % C | % H | % N |
|---|---|---|---|
| Calculated | 68.93 | 8.87 | 16.08 |
| Found | 68.90 | 8.76 | 16.06 |

EXAMPLE 29

(2S,4S)-4-Fluoro-1-({[9-(hydroxymethyl)-3-oxaspiro[5.5]undec-9-yl]-amino}acetyl)-2-pyrrolidinecarbonitrile The expected product is obtained according to the procedure described in Example 1, with the replacement of (2S)-1-(chloroacetyl)-2-pyrrolidinecarbonitrile with (2S,4S)-1-(chloro-acetyl)-4-fluoro-2-pyrrolidinecarbonitrile in Step G.

Elemental Microanalysis:

|  | % C | % H | % N |
|---|---|---|---|
| Calculated | 61.17 | 7.99 | 11.89 |
| Found | 61.63 | 7.87 | 11.47 |

EXAMPLE 30

(2S)-4,4-Difluoro-1-({[9-(hydroxymethyl)-3-oxaspiro[5.5]undec-9-yl]amino}acetyl)-2-pyrrolidinecarbonitrile The expected product is obtained according to the procedure described in Example 1, with the replacement of (2S)-1-(chloroacetyl)-2-pyrrolidinecarbonitrile with (2S)-1-(chloro-acetyl)-4,4-difluoro-2-pyrrolidinecarbonitrile in Step G.

Elemental Microanalysis:

|  | % C | % H | % N |
|---|---|---|---|
| Calculated | 58.21 | 7.33 | 11.31 |
| Found | 58.30 | 7.62 | 11.21 |

EXAMPLE 31

(9-{[2-Oxo-2-(1-pyrrolidinyl)ethyl]amino}-3-oxaspiro[5.5]undec-9-yl)methanol

The expected product is obtained according to the procedure described in Example 1, with the replacement of (2S)-1-(chloroacetyl)-2-pyrrolidinecarbonitrile with 1-(chloroacetyl)-pyrrolidine in Step G.

Elemental Microanalysis:

|  | % C | % H | % N |
|---|---|---|---|
| Calculated | 65.77 | 9.74 | 9.02 |
| Found | 65.75 | 9.62 | 8.85 |

EXAMPLE 32

(4R)-3-({[9-(Hydroxymethyl)-3-oxaspiro[5.5]undec-9-yl]amino}-acetyl)-1,3-thiazolidine-4-carbonitrile The expected product is obtained according to the procedure described in Example 1, with the replacement of (2S)-1-(chloroacetyl)-2-pyrrolidinecarbonitrile with (4R)-3-(chloro-acetyl)-1,3-thiazolidine-4-carbonitrile in Step G.

Elemental Microanalysis:

|  | % C | % H | % N | % S |
|---|---|---|---|---|
| Calculated | 57.76 | 7.70 | 11.89 | 9.07 |
| Found | 57.44 | 7.88 | 11.51 | 8.02 |

EXAMPLE 33

(2S,4S)-4-Hydroxy-1-({[9-(hydroxymethyl)-3-oxaspiro[5.5]undec-9-yl]amino}acetyl)-2-pyrrolidinecarbonitrile The expected product is obtained according to the procedure described in Example 1, with the replacement of (2S)-1-(chloroacetyl)-2-pyrrolidinecarbonitrile with (2S,4S)-1-(chloro-acetyl)-4-hydroxy-2-pyrrolidinecarbonitrile in Step G.

EXAMPLE 34

(2S,4R)-4-Fluoro-1-({[9-(hydroxymethyl)-3-oxaspiro[5.5]undec-9-yl]amino}acetyl)-2-pyrrolidinecarbonitrile trifluoroacetate The expected product is obtained according to the procedure described in Example 1, with the replacement of (2S)-1-(chloroacetyl)-2-pyrrolidinecarbonitrile with (2S,4R)-1-(chloro-acetyl)-4-fluoro-2-pyrrolidinecarbonitrile in Step G.

Elemental Microanalysis:

|  | % C | % H | % N |
|---|---|---|---|
| Calculated | 50.67 | 6.13 | 8.77 |
| Found | 50.47 | 6.05 | 8.47 |

EXAMPLE 35

[9-({2-[(3S)-3-Fluoropyrrolidinyl]-2-oxoethyl}amino)-3-oxaspiro-[5.5]undec-9-yl]methanol The expected product is obtained according to the procedure described in Example 1, with the replacement of (2S)-1-(chloroacetyl)-2-pyrrolidinecarbonitrile with (3S)-1-(chloro-acetyl)-3-fluoropyrrolidine in Step G.

EXAMPLE 36

(9-{[2-Oxo-2-(3,3,4,4-tetrafluoro-1-pyrrolidinyl)ethyl]amino}-3-oxaspiro[5.5]undec-9-yl)methanol The expected product is obtained according to the procedure described in Example 1, with the replacement of (2S)-1-(chloroacetyl)-2-pyrrolidinecarbonitrile with 1-(chloroacetyl)-3,3,4,4-tetrafluoropyrrolidine in Step G.

Elemental Microanalysis:

|  | % C | % H | % N |
|---|---|---|---|
| Calculated | 53.40 | 6.85 | 7.33 |
| Found | 53.83 | 6.67 | 7.18 |

EXAMPLE 37

(2S)-1-({[7-(Hydroxymethyl)spiro[3.5]non-7-yl]amino}acetyl)-2-pyrrolidinecarbonitrile The expected product is obtained according to the procedure described in Example 1, with the replacement of 3-oxaspiro[5.5]undecan-9-one in Step C with the compound obtained in Step B of Example 11.

EXAMPLE 38

(2S)-1-({[8-(Hydroxymethyl)spiro[4.5]dec-8-yl]amino}acetyl)-2-pyrrolidinecarbonitrile The expected product is obtained according to the procedure of Example 1, with the replacement of tetrahydro-2H-pyran-4-carboxaldehyde with cyclopentanecarboxaldehyde in Step A.

EXAMPLE 39

(2S)-1-{[(2,2-Dioxo-2-thiaspiro[3.5]non-7-yl)amino]acetyl}-2-pyrrolidinecarbonitrile The expected product is obtained according to the procedure described in Steps A to D of Example 2, with the replacement of cyclohexanecarboxaldehyde with 3-thietane-carboxaldehyde 1,1-dioxide in Step A.

EXAMPLE 40

(2S)-1-[3-(Spiro[5.5]undec-3-ylamino)propanoyl]-2-pyrrolidine-carbonitrile hydrochloride Step A: (2S)-1-[3-(Spiro[5.5]undec-3-ylamino)propanoyl]-2-pyrrolidinecarbonitrile The expected product is obtained according to the procedure described in Step G of Example 1, starting from the compound obtained in Step C of Example 2 and (2S)-1-(3-chloropropionyl)-2-pyrrolidinecarbonitrile.

Step B: (2S)-1-[3-(Spiro[5.5]undec-3-ylamino)propanoyl]-2-pyrrolidinecarbonitrile hydrochloride The expected product is obtained by converting the compound obtained in the above Step into a salt using hydrochloric acid.

Mass spectrometry: [M+H]+=318.

EXAMPLE 41

(2S)-1-((2RS)-2-{[9-(Hydroxymethyl)-3-oxaspiro[5.5]undec-9-yl]-amino}propanoyl)-2-pyrrolidinecarbonitrile trifluoroacetate The expected product is obtained according to the procedure of Example 1, with the replacement of (2S)-1-(chloroacetyl)-2-pyrrolidinecarbonitrile with (2S)-1-[(2RS)-2-bromopropanoyl]-2-pyrrolidinecarbonitrile in Step G.

Mass spectrometry: [M+H]+=350.

EXAMPLE 42

(2R)-1-({[9-(Hydroxymethyl)-3-oxaspiro[5.5]undec-9-yl]amino}-acetyl)-2-pyrrolidinecarbonitrile The expected product is obtained according to the procedure of Example 1, with the replacement of (2S)-1-(chloroacetyl)-2-pyrrolidinecarbonitrile with (2R)-1-(chloroacetyl)-2-pyrrolidinecarbonitrile in Step G.

Elemental Microanalysis:

|  | % C | % H | % N |
|---|---|---|---|
| Calculated | 64.45 | 8.71 | 12.53 |
| Found | 64.04 | 8.75 | 12.21 |

EXAMPLE 43

(2RS)-4,4-Difluoro-1-({[9-(hydroxymethyl)-3-oxaspiro[5.5]undec-9-yl]amino}acetyl)-2-pyrrolidinecarbonitrile The expected product is obtained according to the procedure of Example 1, with the replacement of (2S)-1-(chloroacetyl)-2-pyrrolidinecarbonitrile with (2RS)-1-(chloroacetyl)-4,4-difluoro-2-pyrrolidinecarbonitrile in Step G.

Elemental Microanalysis:

|  | % C | % H | % N |
|---|---|---|---|
| Calculated | 58.21 | 7.33 | 11.31 |
| Found | 57.46 | 7.41 | 10.94 |

EXAMPLE 44

(2R)-4,4-Difluoro-1-({[9-(hydroxymethyl)-3-oxaspiro[5.5]undec-9-yl]amino}acetyl)-2-pyrrolidinecarbonitrile The expected product is obtained by separation by preparative chiral HPLC chromatography of the racemic compound of Example 43.

Melting point: 128° C.

PHARMACOLOGICAL STUDY OF THE COMPOUNDS OF THE INVENTION

EXAMPLE 45

Inhibition of Dipeptidyl-Peptidase IV in Pig Kidney

Preparation of the Membrane Fraction of Pig Kidney

Pig kidney tissue (large white pig, 2 to 3 months' old) was homogenised (5 g of tissue in 15 ml of Tris buffer (114 mM, pH 7.8-8)) and then centrifuged at 150000×g for 30 min. at 4° C. The pellet was taken up in 15 ml of buffer and re-centrifuged at 150000×g for 30 min. at 4° C. With stirring, the resulting pellet was dissolved in 15 ml of buffer with 60 mM n-octyl-β-glucopyranoside for 30 min. at ambient temperature. After centrifugation at 150000×g for 30 min. at 4° C., the supernatant was dialysed (MWCO 12-14000) against 114 mM Tris pH 7.8-8, and then divided into aliquots at —80° C.

Measurement of Dipetidyl Peptidase IV (DPP IV) Activity

The enzymatic activity is measured by cleavage of a chromogenic substrate, glycyl-prolyl-p-nitroanilide (Gly-Pro-pNA), giving Gly-Pro and pNA (p-nitroaniline); the latter is detected by absorbance at 405 nm. The activity is measured in the absence (control) or in the presence of 10 µl of the inhibitors, using 10 µl of the pig kidney preparation (0.81 mU, 1U=1 µmol of pNA product/min. at 37° C.). Incubation is started by adding the substrate (250 µl), dissolved in Tris buffer (114 mM) pH 7.8-8, over a period of 60 min. at 37° C. For the products dissolved in dimethyl sulphoxide, the final concentration of the latter did not exceed 0.37%. The results were expressed as a percentage of the control, and the $IC_{50}$ values (effective dose for 50% inhibition of the control activity) were determined using non-linear analysis between 0 and 100%, (GraphPad Prism version 4.01 for Windows). Each measurement was carried out in quadruplicate and each $IC_{50}$ determination was carried out from 1 to 5 times.

The results obtained (geometric mean of the $IC_{50}$s) for the compounds representing the invention are compiled in the following Table:

| Compound | $IC_{50}$ DPP IV (nM) |
|---|---|
| Example 1 | 76.1 |
| Example 5 | 68.5 |
| Example 6 | 27.2 |
| Example 8 | 23.0 |
| Example 17 | 43.6 |

-continued

| Compound | IC$_{50}$ DPP IV (nM) |
|---|---|
| Example 18 | 3.5 |
| Example 20 | 73.1 |
| Example 23 | 27.0 |
| Example 28 | 171 |
| Example 29 | 31.6 |
| Example 30 | 20.5 |

The above results show that the compounds of the invention are potent inhibitors of DPP IV.

EXAMPLE 46

Pharmaceutical Composition

| Formulation for the preparation of 1000 tablets each containing a dose of 10 mg | |
|---|---|
| compound of Example 1 | 10 g |
| hydroxypropyl cellulose | 2 g |
| wheat starch | 10 g |
| lactose | 100 g |
| magnesium stearate | 3 g |
| talc | 3 g |

The invention claimed is:

1. A compound selected from those of formula (I):

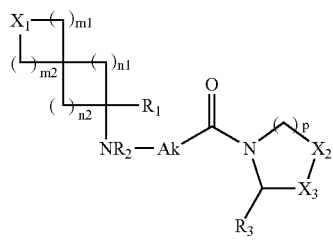

(I)

wherein:
X$_1$ represents an atom or group selected from CR$_{4a}$R$_{4b}$, O, S(O)$_{q1}$ and NR$_5$, wherein R$_{4a}$ and R$_{4b}$, which may be identical or different, each represent hydrogen or linear or branched C$_1$-C$_6$alkyl,
or R$_{4a}$ and R$_{4b}$, together with the carbon atom carrying them, form a C$_3$-C$_7$cycloalkyl group,
q$_1$ represents zero, 1 or 2,
and R$_5$ represents hydrogen or linear or branched C$_1$-C$_6$alkyl optionally substituted by hydroxy,
m$_1$ represents zero or an integer from 1 to 4 inclusive,
m$_2$ represents an integer from 1 to 4 inclusive,
n$_1$ and n$_2$, which may be identical or different, each represent an integer from 1 to 3 inclusive,
R$_1$ represents hydrogen or a group selected from carboxy, linear or branched C$_1$-C$_6$alkoxycarbonyl, carbamoyl optionally substituted by 1 or 2 linear or branched C$_1$-C$_6$alkyl, and linear or branched C$_1$-C$_6$alkyl optionally substituted by hydroxy or by amino optionally substituted by 1 or 2 linear or branched C$_1$-C$_6$alkyl,
R$_2$ represents hydrogen or linear or branched C$_1$-C$_6$alkyl,
Ak represents a linear or branched C$_1$-C$_4$alkylene chain optionally substituted by one or more halogen atoms,
p represents zero, 1 or 2,
R$_3$ represents hydrogen or cyano,
X$_2$ and X$_3$, which may be identical or different, each represent S(O)$_{q2}$, wherein q$_2$ represents zero, 1 or 2, or CR$_{6a}$R$_{6b}$, wherein R$_{6a}$ and R$_{6b}$, which may be identical or different, each represent hydrogen or halogen, or R$_{6a}$ represents hydrogen and R$_{6b}$ represents hydroxy,
its isomers and addition salts thereof with a pharmaceutically acceptable acid.

2. A compound of claim 1, wherein Ak represents a linear or branched C$_1$-C$_4$alkylene chain optionally substituted by one or more fluorine atoms.

3. A compound of claim 1, wherein R$_{6a}$ and R$_{6b}$, which may be identical or different, each represent hydrogen or fluorine.

4. A compound of claim 1, wherein X$_1$ represents oxygen or —CH$_2$—.

5. A compound of claim 1, wherein m$_1$ and m$_2$ each represent 1 or 2.

6. A compound of claim 1, wherein n$_1$ and n$_2$ each represent 1 or 2 and are identical.

7. A compound of claim 1, wherein

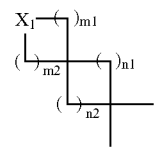

represents a group selected from

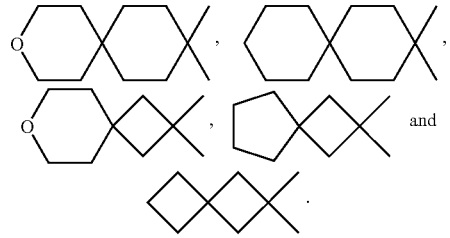

8. A compound of claim 1, wherein R$_2$ represents hydrogen.

9. A compound of claim 1, wherein Ak represents —CH$_2$—.

10. A compound of claim 1, wherein p represents 1.

11. A compound of claim 1, wherein R$_3$ represents cyano.

12. A compound of claim 1, wherein X$_2$ represents CR$_{6a}$R$_{6b}$.

13. A compound of claim 1, wherein X$_3$ represents CR$_{6a}$R$_{6b}$.

14. A compound of claim 11 in which the configuration of the carbon carrying the R$_3$ group is (S).

15. A compound of claim 12, in which the configuration of the carbon carrying the R$_3$ group is (S).

16. A compound of claim 13, in which the configuration of the carbon carrying the R$_3$ group is (S).

17. A compound of claim 11, wherein X$_2$ or X$_3$ represents a S(O)$_{q2}$ group and the configuration of the carbon carrying the R$_3$ group is (R).

18. A compound of claim 1 which is selected from:
- (2S)-1-({[9-(hydroxymethyl)-3-oxaspiro[5.5]undec-9-yl]amino}acetyl)-2-pyrrolidinecarbonitrile, and its addition salts with a pharmaceutically acceptable acid;
- (2S)-1-({[3-(hydroxymethyl)spiro[5.5]undec-3-yl]amino}acetyl)-2-pyrrolidine-carbonitrile, and its addition salts with a pharmaceutically acceptable acid;
- (2S)-1-({[2-(hydroxymethyl)spiro[3.4]oct-2-yl]amino}acetyl)-2-pyrrolidine-carbonitrile, and its addition salts with a pharmaceutically acceptable acid;
- (4R)-3-[(spiro[5.5]undec-3-ylamino)acetyl]-1,3-thiazolidine-4-carbonitrile, and its addition salts with a pharmaceutically acceptable acid;
- 2-({2-[(2S)-2-cyanopyrrolidinyl]-2-oxoethyl}amino)spiro[3.3]heptane-2-carboxamide, and its addition salts with a pharmaceutically acceptable acid;
- (2S)-1-({[(2-(hydroxymethyl)-7-oxaspiro[3.5]non-2-yl]amino}acetyl)-2-pyrrolidinecarbonitrile, and its addition salts with a pharmaceutically acceptable acid;
- (2S,4S)-4-fluoro-1-({[9-(hydroxymethyl)-3-oxaspiro[5.5]undec-9-yl]amino}-acetyl)-2-pyrrolidinecarbonitrile, its (2S,4R) isomer, its (2R, 4R) isomer and addition salts thereof with a pharmaceutically acceptable acid;
- (2S)-4,4-difluoro-1-({[9-(hydroxymethyl)-3-oxaspiro[5.5]undec-9-yl]amino}-acetyl)-2-pyrrolidinecarbonitrile, and its addition salts with a pharmaceutically acceptable acid;
- and (4R)-3-({[9-(hydroxymethyl)-3-oxaspiro[5.5]undec-9-yl]amino}acetyl)-1,3-thiazolidine-4-carbonitrile, and its addition salts with a pharmaceutically acceptable acid.

19. A pharmaceutical composition comprising as active ingredient a compound of claim 1 in combination with one or more pharmaceutically acceptable, inert, non-toxic carriers.

20. A method of treating a living animal body, including a human, afflicted with glucose intolerance or with a disorder associated with hyperglycaemia, comprising the step of administering to the living animal body, including a human, an amount of a compound of claim 1 which is effective for alleviation of the condition.

21. A method of treating a living animal body, including a human, afflicted with type II diabetes, comprising the step of administering to the living animal body, including a human, an amount of a compound of claim 1 which is effective for alleviation of type II diabetes.

* * * * *

UNITED STATES PATENT AND TRADEMARK OFFICE
CERTIFICATE OF CORRECTION

PATENT NO. : 7,439,263 B2 Page 1 of 1
APPLICATION NO. : 11/131510
DATED : October 21, 2008
INVENTOR(S) : Guillaume DeNanteuil et al.

It is certified that error appears in the above-identified patent and that said Letters Patent is hereby corrected as shown below:

Title Page; item (56);
References: Please add  "EP 1308439 - 5/2003"
"European Search Report for EP05291066.8 of 8/2005"

Signed and Sealed this

Fifth Day of May, 2009

JOHN DOLL
*Acting Director of the United States Patent and Trademark Office*